(12) United States Patent
Smolak et al.

(10) Patent No.: US 10,184,878 B2
(45) Date of Patent: *Jan. 22, 2019

(54) FLOW CYTOMETER SIGNAL PEAK IDENTIFICATION EMPLOYING DYNAMIC THRESHOLDING

(71) Applicant: IntelliCyt Corporation, Albuquerque, NM (US)

(72) Inventors: Andrew W. Smolak, Golden, CO (US); Jean-Luc Fraikin, Toronto (CA); Erica Dawson Tenent, Broomfield, CO (US); Kathy L. Rowlen, Longmont, CO (US)

(73) Assignee: IntelliCyt Corporation, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/871,731

(22) Filed: Jan. 15, 2018

(65) Prior Publication Data
US 2018/0136108 A1 May 17, 2018

Related U.S. Application Data

(63) Continuation of application No. 15/316,427, filed as application No. PCT/US2015/033907 on Jun. 3, 2015, now Pat. No. 9,903,803.
(Continued)

(51) Int. Cl.
*G01N 15/14* (2006.01)
*G01N 15/10* (2006.01)

(52) U.S. Cl.
CPC ..... *G01N 15/1429* (2013.01); *G01N 15/1459* (2013.01); *G01N 2015/1006* (2013.01); *G01N 2015/1461* (2013.01)

(58) Field of Classification Search
CPC .............................. G01N 15/14; G01N 21/00
(Continued)

(56) References Cited

U.S. PATENT DOCUMENTS 3,516,629 A   6/1970   Say
3,758,058 A   9/1973   Neudeck et al.
(Continued)

FOREIGN PATENT DOCUMENTS

CA    2796489 A1    5/2014
EP    0822404 A2    4/1998
(Continued)

*Primary Examiner* — Roy M Punnoose
(74) *Attorney, Agent, or Firm* — Marsh Fischmann & Breyfogle LLP; Thomas R. Marsh

(57) ABSTRACT

Methods of evaluating particle attributes in a sample fluid subjected to flow cytometry investigation in a flow cytometer instrument, methods of processing time series signal data traces output by a flow cytometer instrument, and a flow cytometer system are provided. In the methods and systems, data points comprising time series signal data traces corresponding with detection during the flow cytometry investigation of light from the sample fluid in one or more wavelength ranges indicative of the presence of one or more particle attributes in the sample fluid are batch-processed using a batch-specific signal peak threshold determined as a function of a batch-specific noise characteristic to identify signal peaks in the batch of data points indicative of the presence of the one or more particle attributes in the sample fluid.

19 Claims, 11 Drawing Sheets

Related U.S. Application Data

(60) Provisional application No. 62/008,345, filed on Jun. 5, 2014.

(58) Field of Classification Search
USPC .......................................................... 356/441
See application file for complete search history.

(56) References Cited

U.S. PATENT DOCUMENTS

| | | | |
|---|---|---|---|
| 5,386,962 | A | 2/1995 | Adriance et al. |
| 7,069,191 | B1 | 6/2006 | Moore |
| 9,546,936 | B2 | 1/2017 | Rowlen et al. |
| 2006/0134002 | A1* | 6/2006 | Lin .................. A61K 49/0032 424/9.6 |
| 2006/0259253 | A1 | 11/2006 | Ellison et al. |
| 2008/0021674 | A1 | 1/2008 | Puskas |
| 2010/0284016 | A1 | 11/2010 | Teitell et al. |
| 2011/0024615 | A1 | 2/2011 | Tanner et al. |
| 2011/0089328 | A1 | 4/2011 | Li |
| 2012/0070818 | A1 | 3/2012 | Rowlen et al. |
| 2013/0171683 | A1 | 7/2013 | Durack et al. |
| 2013/0252237 | A1 | 9/2013 | Wagner |
| 2013/0338968 | A1* | 12/2013 | Hanashi ............ G01N 21/6458 702/189 |

FOREIGN PATENT DOCUMENTS

| | | | |
|---|---|---|---|
| EP | 1002968 | A2 | 5/2000 |
| EP | 1176412 | A2 | 1/2002 |
| WO | 2014062719 | A2 | 4/2014 |

* cited by examiner

FLOW CYTOMETER SIGNAL PEAK IDENTIFICATION EMPLOYING DYNAMIC THRESHOLDING

RELATED APPLICATIONS

This application is a continuation of U.S. patent application Ser. No. 15/316,427, filed Dec. 5, 2016, entitled "FLOW CYTOMETER SIGNAL PEAK IDENTIFICATION EMPLOYING DYNAMIC THRESHOLDING," which is a U.S. National Stage of International Patent Application No. PCT/US2015/033907, filed Jun. 3, 2015, entitled "FLOW CYTOMETER SIGNAL PEAK IDENTIFICATION EMPLOYING DYNAMIC THRESHOLDING," which claims the benefit of priority to U.S. Provisional Patent Application No. 62/008,345, filed Jun. 5, 2014, entitled "FLOW CYTOMETER SIGNAL PEAK IDENTIFICATION EMPLOYING DYNAMIC THRESHOLDING," all of which foregoing patent applications are incorporated herein by reference in their entirety.

FIELD OF THE INVENTION

The present invention relates generally to the processing of data signal traces output by a flow cytometer instrument, and more particularly, to the identification of signal peaks within data signal traces output by a flow cytometer instrument.

BACKGROUND OF THE INVENTION

Flow cytometry is an analytical technique used in a number of applications to measure physical and/or chemical properties of biological or nonbiological particles as they flow in a sample fluid, often an aqueous liquid medium, through an investigation cell (also referred to herein as a flow cell). Flow through the cell may be investigated by a variety of techniques, including subjecting the flow to electrical, acoustic and/or optical signals in measuring and analyzing responses to detect and evaluate particles in the sample.

When attempting to evaluate whether or not a particular particle is present in a sample fluid, one or more fluorescent stains or dyes may be added to the sample fluid. The dyes or stains are selected to fix on the particle of interest and to fluoresce when exposed to excitation light within a particular range of wavelengths. The fluorescent response light from the sample fluid may be detected by one or more photodetectors of the flow cytometry instrument, which in turn, generate one or more electrical signal data traces in which the voltage level at a particular instant in time indicates the level of fluorescent response light received by the detector from the sample fluid at that time. By identifying peaks in the signal data traces, an evaluation may be made regarding the presence of the target particle in the sample fluid. However, identifying valid signal peaks in signal data traces of a flow cytometer instrument can be challenging, particularly where two or more stains or dyes are used in the flow cytometry investigation which may result in cross-talk among signal data traces corresponding with a fluorescent response resulting from each stain or dye.

SUMMARY OF THE INVENTION

Accordingly, methods of evaluating particle attributes in a sample fluid subjected to flow cytometry investigation in a flow cytometer instrument, methods of processing time series signal data traces output by a flow cytometer instrument, and a flow cytometer system are provided. In the methods and systems, data points comprising time series signal data traces corresponding with detection during the flow cytometry investigation of light from the sample fluid in one or more wavelength ranges indicative of the presence of one or more particle attributes in the sample fluid are batch-processed using a batch-specific signal peak threshold determined as a function of a batch-specific noise characteristic to identify signal peaks in the batch of data points indicative of the presence of the one or more particle attributes in the sample fluid.

In one aspect, a method of evaluating particle attributes in a sample fluid subjected to flow cytometry investigation in a flow cytometer instrument may include processing flow cytometry investigation response data generated by the flow cytometer instrument. The response data may comprise a time series signal data trace corresponding with detection during the flow cytometry investigation of light from the sample fluid in a wavelength range that is indicative of the presence of a particle attribute in the sample fluid. The processing may comprise separately batch processing a plurality of different time interval batches of data points of the time series signal data trace. The batch processing of each batch of data points may comprise: (1) determining a batch-specific noise characteristic for the batch of data points; (2) determining a batch-specific signal peak threshold for the batch of data points as a function of the batch-specific noise characteristic; and (3) identifying signal peaks in the batch of data points indicative of the presence of the particle attribute in the sample fluid using threshold criteria including the batch-specific signal peak threshold.

In one particular implementation of the method where the flow cytometry investigation involves two stains or dyes and hence two fluorescent responses of differing wavelength ranges, the time series signal data trace may comprise a first time series signal data trace, the particle attribute may comprise a first particle attribute, the light may comprise first light from the sample fluid in a first wavelength range that is indicative of the presence of the first particle attribute, the response data may further comprise a second time series signal data trace corresponding with detection during the flow cytometry investigation of second light from the sample fluid in a second wavelength range that is indicative of the presence of a second particle attribute in the sample fluid, and the method may further comprise separately batch processing a plurality of different time interval batches of data points of the second time series signal data trace. Time intervals of each successive batch of data points of the second time series signal data trace may correspond in time with time intervals of each successive batch of data points of the first time series signal data trace. The batch processing of each batch of data points of the second time series signal data trace may comprise: (1) determining a batch-specific noise characteristic for the batch of data points of the second time series signal data trace; (2) determining a batch-specific signal peak threshold for the batch of data points of the second time series signal data trace as a function of the batch-specific noise characteristic for the batch of data points of the second time series signal data trace; and (3) identifying signal peaks in the batch of data points of the second time series signal data trace indicative of the presence of the second particle attribute in the sample fluid using threshold criteria including the batch-specific signal peak threshold.

In another aspect, a method of processing time series signal data traces output by a flow cytometer instrument may include selecting a batch of data points from each of a first and a second time series signal data trace output by the flow cytometer instrument. The first time series signal data trace may comprise a first plurality of data points corresponding with detection by the flow cytometer instrument of light in a first wavelength range that is indicative of the presence of a first particle attribute in a sample fluid subjected to flow cytometry investigation in the flow cytometer instrument, and the second time series signal data trace may comprise a second plurality of data points corresponding with detection by the flow cytometer instrument of light in a second wavelength range that is indicative of the presence of a second particle attribute in the sample fluid. The method may also include separately processing each batch of selected data points from each of the first and second time series signal data traces. The batch-processing of each batch of data points may comprise: (1) determining a batch-specific noise characteristic for the batch of data points; (2) determining a batch-specific signal peak threshold for the batch of data points as a function of the batch-specific noise characteristic; and (3) identifying signal peaks in the batch of data points indicative of the presence of one of the first particle attribute or the second particle attribute in the sample fluid using threshold criteria including the batch-specific signal peak threshold. The method may also include comparing times of occurrence of the identified signal peaks in the separately batch processed batches of data points of the first and the second time series signal data traces, and recording as the presence of a target particle a temporal coincidence of identified signal peaks in the batches of data points of the first and the second time series signal data traces.

In a further aspect, a flow cytometer system may include a flow cytometer instrument operable to output flow cytometry investigation response data. The response data may comprise a time series signal data trace corresponding with detection during the flow cytometry investigation of light from the sample fluid in a wavelength range that is indicative of the presence of a particle attribute in the sample fluid. The flow cytometer instrument may also include a processor operable to receive the flow cytometry response data output by the flow cytometer instrument. The processor may be further operable to separately batch process a plurality of different time interval batches of data points of the time series signal data trace to: (1) determine a batch-specific noise characteristic for the batch of data points; (2) determine a batch-specific signal peak threshold for the batch of data points as a function of the batch-specific noise characteristic; and (3) identify signal peaks in the batch of data points indicative of the presence of the particle attribute in the sample fluid using threshold criteria including the batch-specific signal peak threshold.

In one particular implementation of the system where the flow cytometry investigation involves two stains or dyes and hence two fluorescent responses of differing wavelength ranges, the time series signal data trace may comprise a first time series signal data trace, the particle attribute may comprise a first particle attribute, the light may comprise first light from the sample fluid in a first wavelength range that is indicative of the presence of the first particle attribute, the response data may further comprise a second time series signal data trace corresponding with detection during the flow cytometry investigation of light from the sample fluid in a second wavelength range that is indicative of the presence of a second particle attribute in the sample fluid, and the processor may be further operable to separately batch process a plurality of different time interval batches of data points of the second time series signal data trace. Time intervals of each successive batch of data points of the second time series signal data trace may correspond in time with time intervals of each successive batch of data points of the first time series signal data trace. The processor may separately batch processes the plurality of different time interval batches of data points of the second time series signal data trace to: (1) determine a batch-specific noise characteristic for the batch of data points of the second time series signal data trace; (2) determine a batch-specific signal peak threshold for the batch of data points of the second time series signal data trace as a function of the batch-specific noise characteristic for the batch of data points of the second time series signal data trace; and (3) identify signal peaks in the batch of data points of the second time series signal data trace indicative of the presence of the second particle attribute in the sample fluid using threshold criteria including the batch-specific signal peak threshold.

Various refinements exist of the features noted in relation to the various aspects of the present invention. Further features may also be incorporated in the various aspects of the present invention. These refinements and additional features may exist individually or in any combination, and various features of the various aspects may be combined. These and other aspects and advantages of the present invention will be apparent upon review of the following Detailed Description when taken in conjunction with the accompanying figures.

DETAILED DESCRIPTION

Figure 1A:
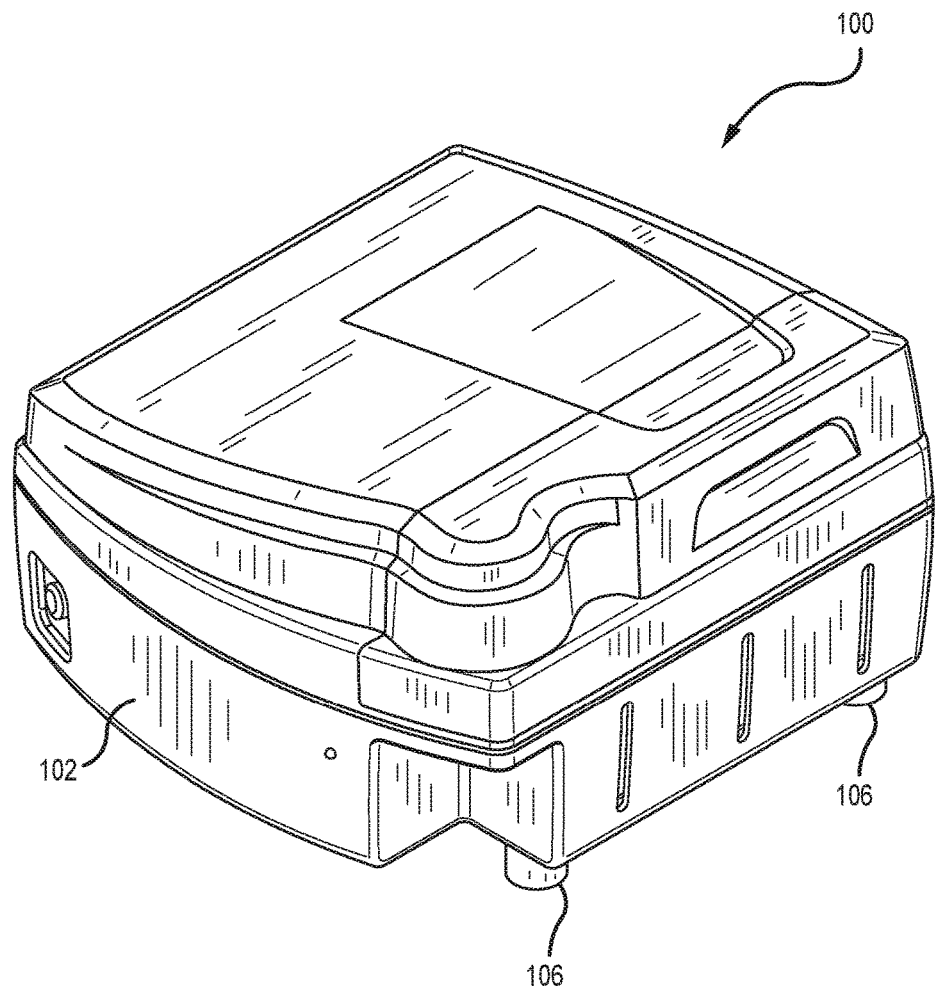
FIGS. 1A-1B are perspective and side views of one embodiment of a flow cytometer instrument.
Figure 1B:
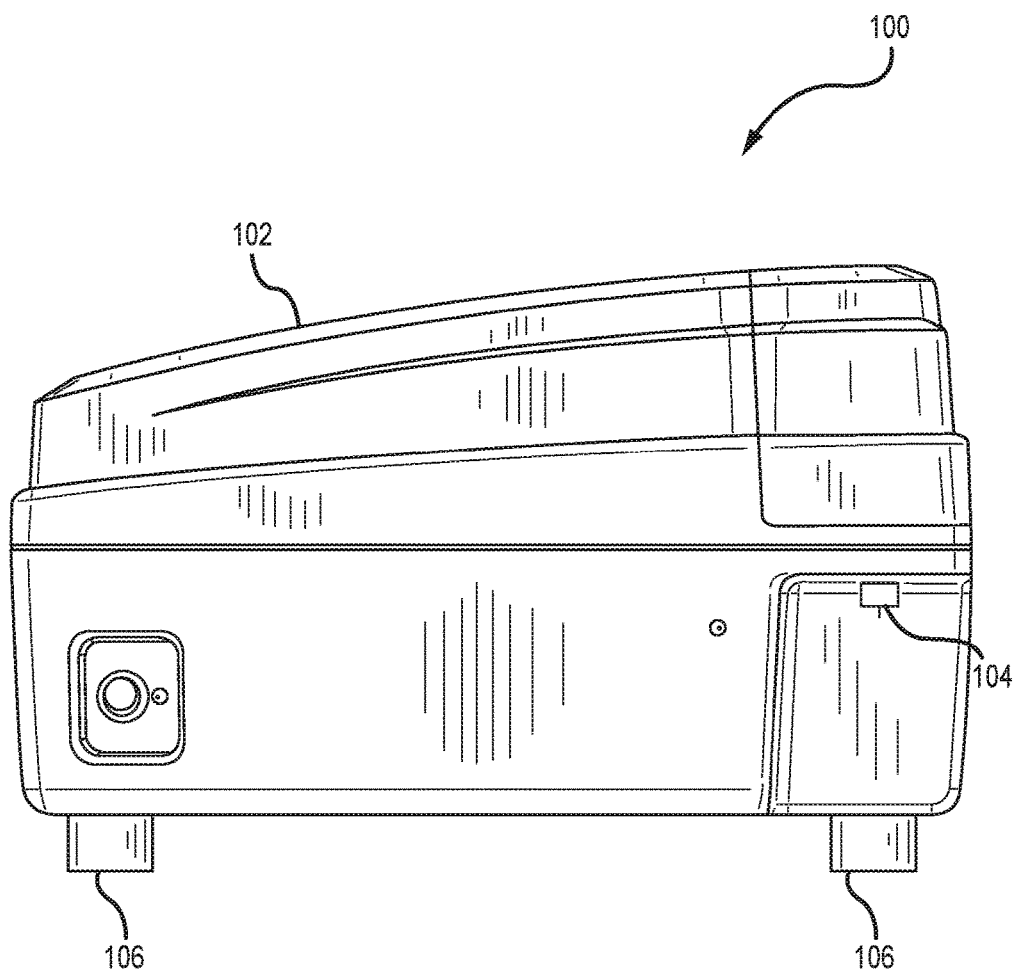

FIGS. 1A-1B show a flow cytometer 100 that includes flow cytometry componentry contained within a protective enclosure 102. Fluid samples may be introduced into the flow cytometer 100 for flow cytometry investigation through a sample inlet 104. The flow cytometer 100 includes support pads 106 on which the weight of the enclosure 102 and contents within the enclosure 102 are supported. Advantageously, the support pads 106 may be of a material that provides significant vibration isolation to the enclosure 102, and to contents within the enclosure 102, from ambient environment vibrations that may be transmitted through a shelf, table or other surface on which the flow cytometer 100 may be situated during use. The support pads 106 may, therefore, provide a vibration isolation structure that provides a vibration propagation barrier to the enclosure 102 and contents within the enclosure 102. For example, the support pads 106 may be of a polymeric composition that provides a vibration decomposing effect. Example polymeric compositions include thermoplastic and thermoset polymer compositions.

Figure 2A:
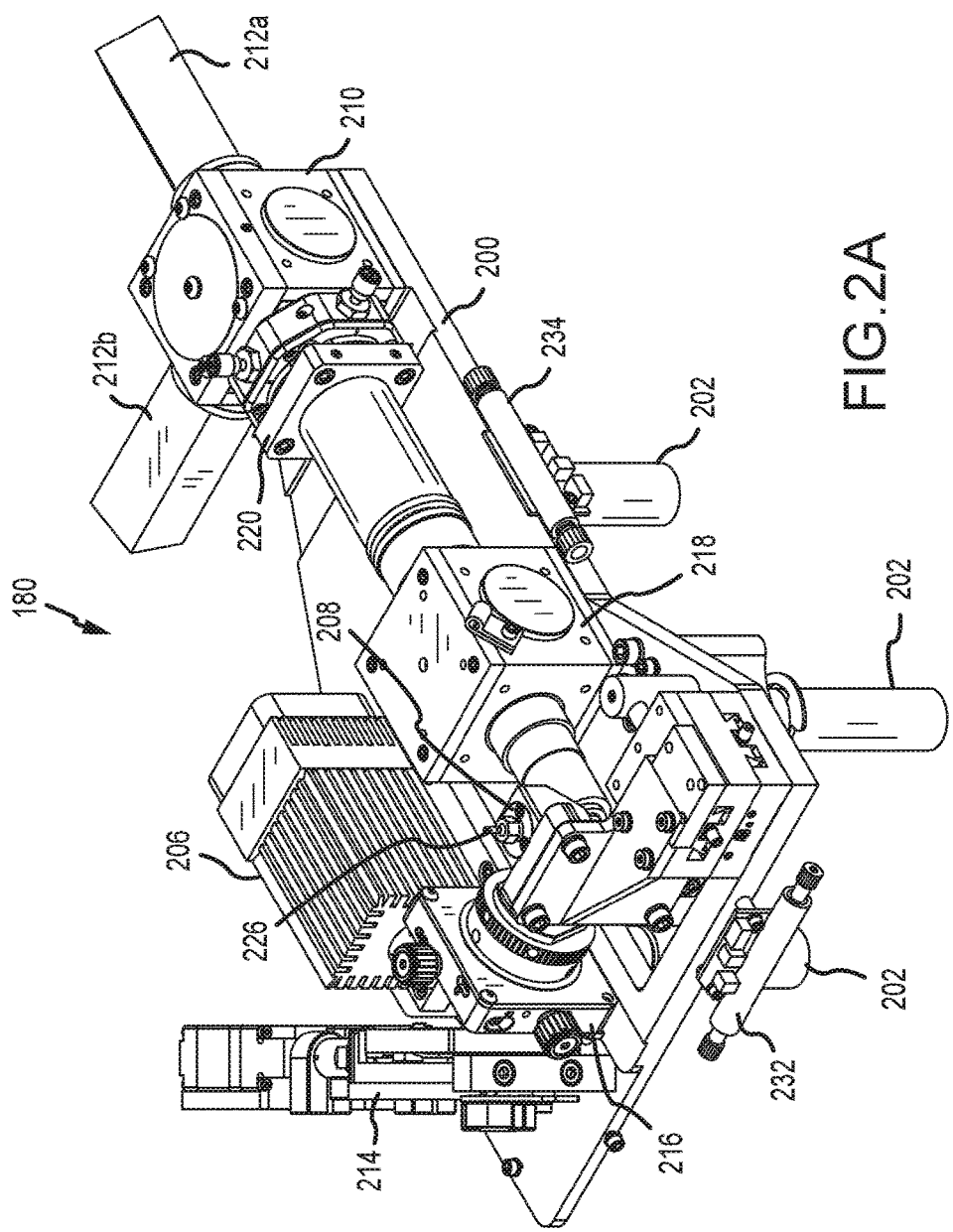
FIGS. 2A-2B are perspective and top views of one embodiment of a flow cytometer internal assembly that may be included within the flow cytometer instrument of FIGS. 1A-1B.
Figure 2B:
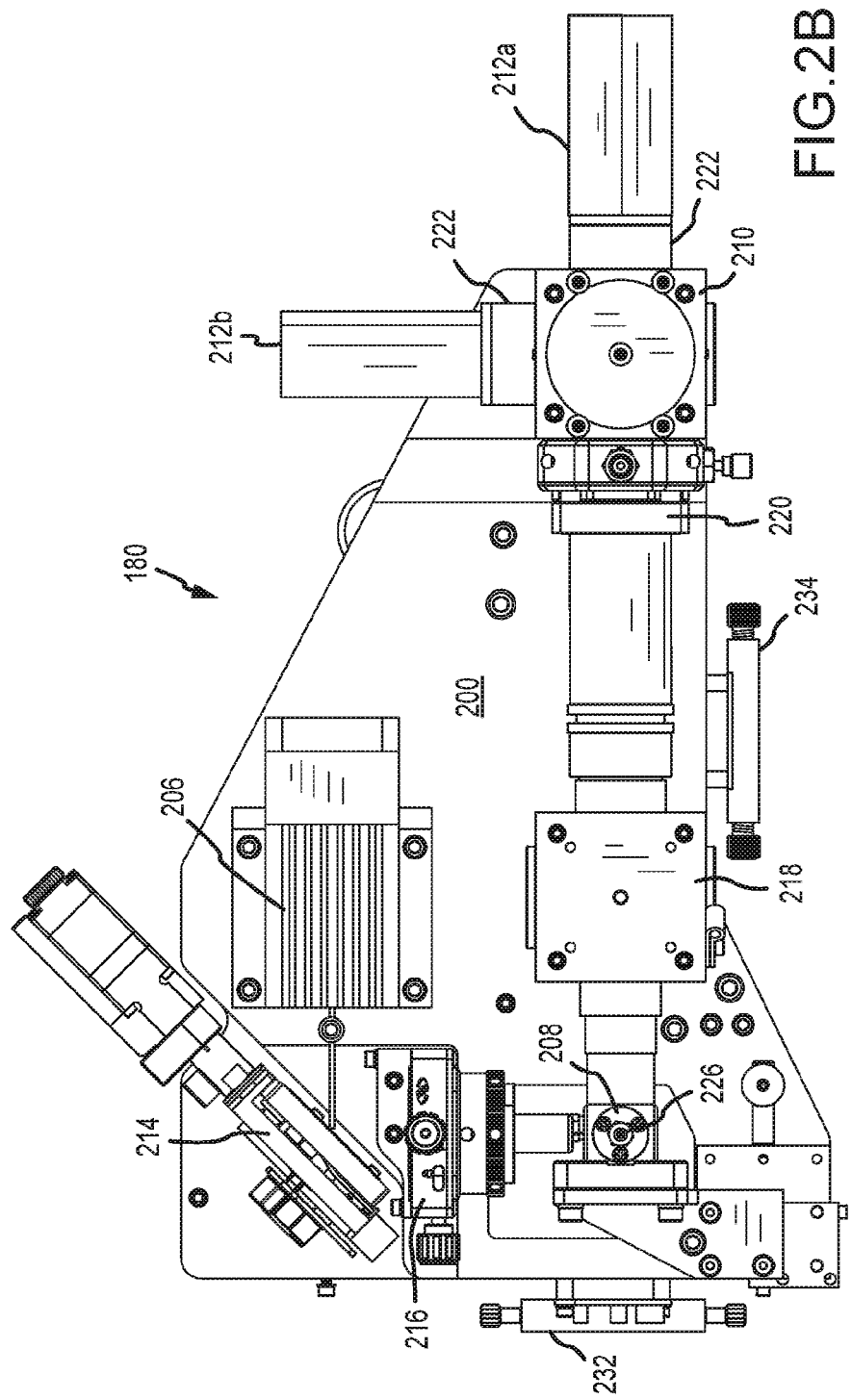

FIGS. 2A-2B show an example flow cytometer internal assembly 180 that may be disposed within the enclosure 102 of the flow cytometer 100. The internal assembly 180 includes a flow optical system assembly including support platform 200 and a number of flow cytometry optical components supported by the support platform 200, with the optical components having fixed relative positioning configured for performing flow cytometry investigations of sample fluids. The flow cytometry optical system assembly is supported by a support structure including three rigid support members 202 and vibration isolation mounts (not shown in FIGS. 2A-2B) that are supported by the support members 202, and on which the entire weight of the support platform 200 and components supported by the support platform 200 are supported during flow cytometry investigation operations.

The flow cytometry optical components supported by the support platform 200 include a light source in the form of a laser unit 206, a flow cell unit 208 and a light detection system including a dichroic mirror unit 210 and two light detector units 212, for example which may include photomultiplier tubes. During operation of a flow cytometry investigation of sample fluid flowing through an investigatory flow path of a flow cell of the flow cell unit 208, light from the laser unit 206 travels along a first optical path to the flow cell. The first optical path includes a mirror unit 214 that includes a mirror that reflects light from the laser unit 206 to direct that light through a focusing lens 216 to focus light in the vicinity of the investigatory flow path within the flow cell of the flow cell unit 208. Light from the investigatory flow path of the flow cell is directed along a second optical path from the flow cell to the dichroic mirror unit 210 for detection by the light detectors 212. The second optical path includes a focusing lens unit 218 and a spatial lens unit 220 between the flow cell unit 208 and the dichroic mirror unit 210. A dichroic mirror within the dichroic mirror unit 210 splits the light between light that passes through the dichroic mirror and is directed toward light detector 212a and light that is reflected by the dichroic mirror and is directed toward light detector 212b. Band-pass filters 222 may be disposed in the optical paths to the light detectors 212 to pass a narrow light including a wavelength or band of wavelengths targeted for detection by the respective light detectors 212a, 212b.

During operation of the flow cytometer 100 to perform a flow cytometry investigation of a fluid sample, the fluid sample to be investigated may be introduced into the flow cytometer through the sample inlet 104. The sample fluid is conducted to an inlet (not shown in FIGS. 2A-2B) to the flow cell unit 208. The sample fluid flows through the investigatory fluid path in the flow cell unit 208 and exits the flow cell unit 208 through a sample exit 226. Sample fluid introduced into the flow cell unit 208 through the sample fluid inlet flows through a transparent section of the flow cell unit 208 where it is subjected to incident light from the laser unit 206 and exits through the sample exit 226. The investigatory flow path passes through the transparent section. The transparent section may, for example, be made of a quartz crystal material. Between the sample inlet 104 of the flow cytometer 100 and the inlet to the flow cell unit 208, the fluid sample passes through a fluid path (not shown) that includes a flow meter 232 where the flow rate of the fluid sample may be measured for data collection purposes as part of a feedback control mechanism for controlling the fluid sample flow rate to the flow cell unit 208. In the flow cell unit 208, a sheath fluid is introduced around the fluid sample flow before the fluid sample flows through the transparent section for investigation. The sheath fluid is introduced into the flow cell unit 208 through a sheath fluid inlet (not shown in FIGS. 2A-2B). Prior to introduction of the sheath fluid into the flow cell unit 208, the sheath fluid passes through a fluid path (not shown in FIGS. 2A-2B) that includes a flow sensor 234 for monitoring of the sheath fluid flow rate to the flow cell unit 208 and for use for feedback control to control the flow rate of the sheath fluid to the flow cell unit 208. The flow sensors 232 and 234 are conveniently supported on the support platform 200.

Figure 3:
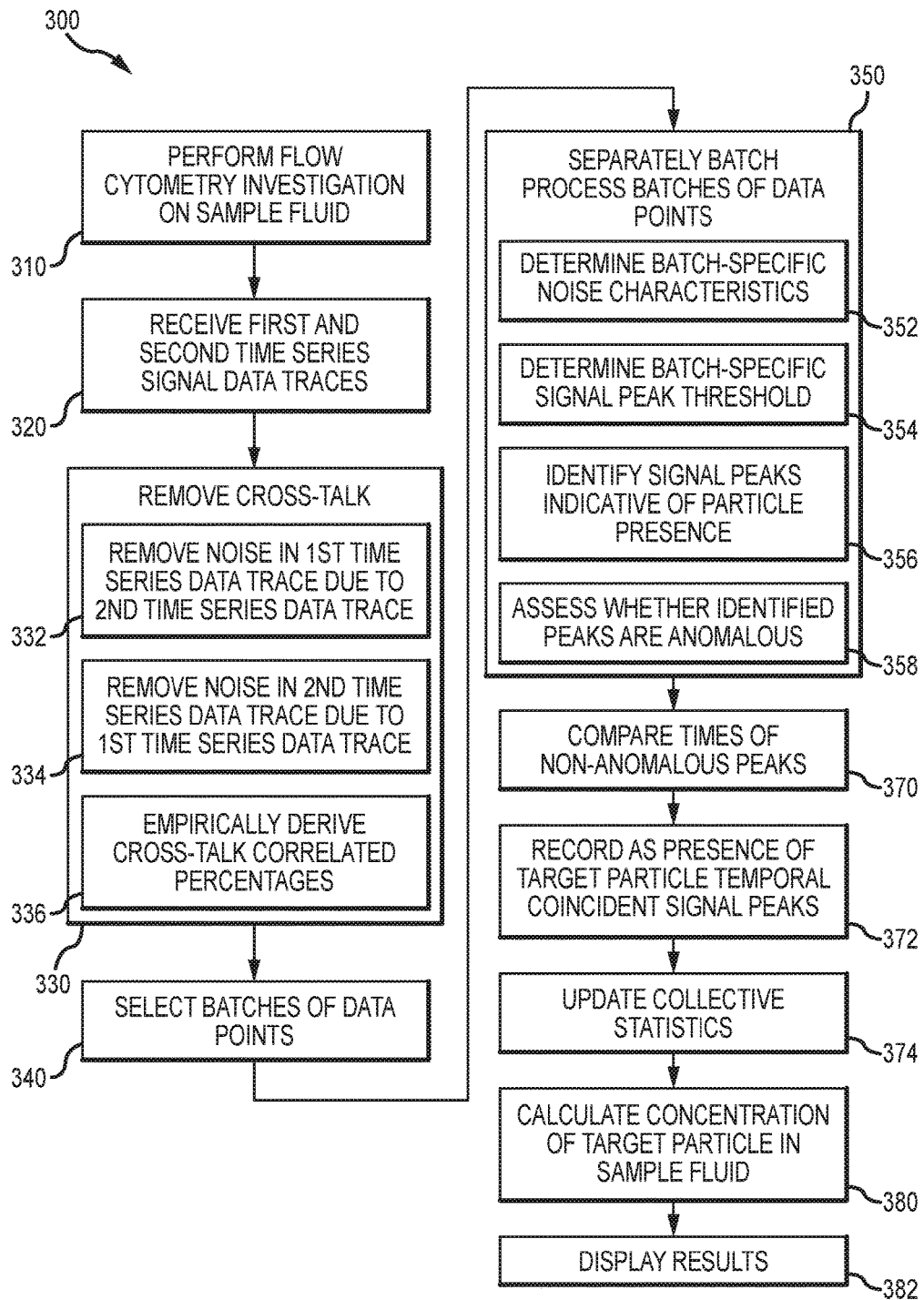
FIG. 3 is a flow diagram depicting the steps of one embodiment of a method of evaluating particle attributes in a sample fluid subjected to flow cytometry investigation in a flow cytometer.

FIG. 3 illustrates steps that may be included in a method of evaluating particle attributes in a sample fluid subjected to flow cytometry investigation in a flow cytometer instrument such as flow cytometer 100 of FIGS. 1A-1B having a flow cytometer internal assembly 180 such as depicted in FIGS. 2A-2B.

The method 300 may be initiated with step 310 in which a flow cytometry investigation is performed on a sample fluid. In this regard, a flow cytometer 100 such as depicted in FIGS. 1A-1B may be used to perform the flow cytometry investigation. Performance of the flow cytometry investigation may involve directing the sample fluid through a flow cell in which the sample fluid is subjected to an excitation light from at least one light source, and detecting separately response light in at least two different wavelength ranges emitted from the sample fluid in the flow cell. In this regard, the sample fluid may be directed through a flow cell unit 208 of a flow cytometer internal assembly 180 such as depicted in FIGS. 2A-2B with the laser unit 206 light source providing the excitation light to the flow cell unit 208 via the mirror unit 214 and focusing lens 216 in the first optical path, and the detectors 212a, 212b separately detecting the response light emitted from the sample fluid and directed thereto from the flow cell unit 208 via focusing lens unit 218, the spatial lens unit 220, and the dichroic mirror 210.

Step 310 may be undertaken at various times in relation to one or more other steps of the method 300. For example, in some implementations, step 310 may be undertaken immediately prior to undertaking other steps of the method 300, in some implementations, step 310 may be undertaken contemporaneously with undertaking one or more other steps of the method 300, and, in some implementations, step 310 may be undertaken well in advance of undertaking other steps of the method 300.

In step 320, flow cytometry response data resulting from the flow cytometry investigation is received. In this regard, the flow cytometry response data may be received from the optical detector(s) 212a, 212b of the flow cytometry internal assembly 180 at a processor (not shown in FIGS. 2A-2B) that may be included within a flow cytometer such as depicted in FIGS. 1A-1B and/or at a processor that is part of a separate computer system that is in communication (e.g. via a wired connection such as universal serial bus connection, a parallel port connection, an Ethernet connection or the like or a wireless connection such as a WiFi data connection, a cellular data connection, or the like).

The flow cytometry response data may comprise one or more time series signal data traces. Each time series signal data trace may comprise a plurality of data points corresponding with detection during the flow cytometry investigation of light from the sample fluid in a wavelength range that is indicative of the presence of a particle attribute in the sample fluid. In one implementation, there may be first and second times series signal data traces, with the first time series signal data trace comprising a first plurality of data points corresponding with detection during the flow cytometry investigation of first light from the sample fluid in a first wavelength range that is indicative of the presence of a first particle attribute in the sample fluid and the second time series signal data trace comprising a second plurality of data points corresponding with detection during the flow cytometry investigation of second light from the sample fluid in a second wavelength range that is indicative of the presence of a second particle attribute in the sample fluid. In this regard, the first particle attribute may comprise presence of nucleic acid and the second particle attribute may comprise presence of protein. Thus, the first time series signal data trace may be referred to herein as the nucleic acid channel or N-channel and the second time series signal data trace may be referred to herein as the protein channel or P-channel. The first light may comprise light in the first wavelength range that is a fluorescent emission of a first fluorescent stain, and the second light may comprise light in a second wavelength range that is a fluorescent emission of a second fluorescent stain.

In step 330, cross-talk is removed from the first and second time series signal data traces.

In one implementation, the removal of cross-talk may proceed in accordance with steps 332, 334 and 336, and, as depicted in FIG. 3, the step 330 of removing cross-talk may be undertaken prior to proceeding with subsequent steps of method 300. In other implementations, all or some part of the step 330 of removing cross-talk (e.g., one or more of steps 332, 334, 336) may be undertaken contemporaneously with one or more subsequent steps of method 300 (e.g., contemporaneously with step 350 of separate batch processing of each batch of data points as described hereinbelow). Regardless of when the step 330 of cross-talk removal occurs, cross-talk removal generally involves reducing 332 the magnitude of each data point comprising the first time series signal data trace in accordance with a correlated percentage of a magnitude of the second time series signal data trace and reducing 334 the magnitude of each data point comprising the second time series signal data trace in accordance with a correlated percentage of a magnitude of the first time series signal data trace. The correlated percentage of the magnitude of the first time series signal data trace may comprise a first empirically derived cross-talk percentage, and the correlated percentage of the magnitude of the second time series signal data trace may comprise a second empirically derived cross-talk percentage.

Figure 4:
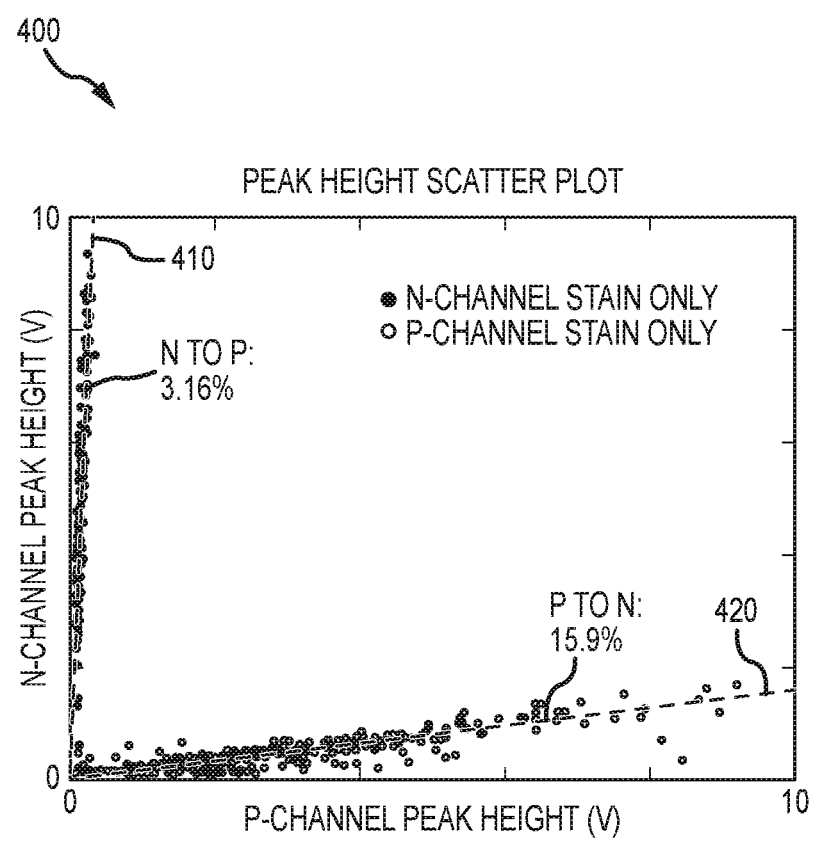
FIG. 4 is a scatter plot of peak heights for a first time series signal data trace versus peak heights for a second time series signal data trace.

Referring to FIG. 4, one manner of deriving 336 the respective first and second cross-talk percentages may, for example, involve processing a single-stain sample fluid appropriate for nucleic acid detection through a flow cytometer instrument to obtain N-channel data, and also processing a single-stain sample fluid appropriate for protein detection through a flow cytometer instrument to obtain P-channel data. As depicted in the scatter plot 400 of FIG. 4, peak heights for the N-channel data may then be plotted versus peak heights for the P-channel data, and respective N-channel and P-channel best fit lines 410, 420 through the origin may be calculated from the N-channel peak height and P-channel peak height data. The slope of the N-channel best fit line 410 yields the ratio of peak heights and thus the N-to-P cross-talk percentage (3.16% for the exemplary data plotted in FIG. 4), and the slope of the P-channel best fit line 420 yields the ratio of peak heights and thus the P-to-N cross-talk percentage (15.9% for the exemplary data plotted in FIG. 4). The step 336 of deriving the cross-talk percentages may take place prior to the steps 332, 334 of reducing the magnitudes of the data points comprising the first and second times series signal data traces. In this regard, the cross-talk percentage derivation step 336 may be undertaken for a particular model instrument intended for investigating a particular category of particle (e.g. a flu virus) so that the respective cross-talk percentages can be provided as a parameter that may be included within such models of flow cytometer instrument at the time of manufacture or entered by a user prior to use of the instrument in the field.

Figure 5A:
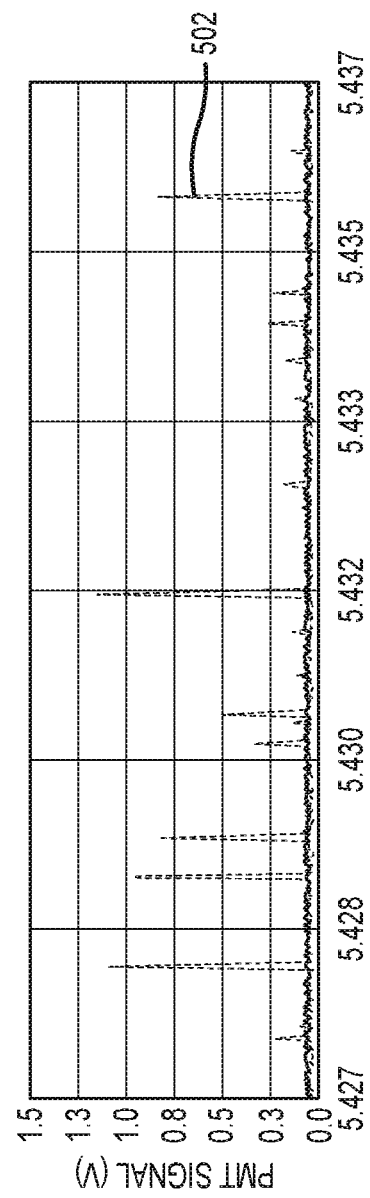
FIGS. 5A-5B are plots of exemplary corrected first and second time series signal data traces following removal of cross-talk.

FIG. 5A depicts an exemplary corrected N-channel signal data trace 502 in which cross-talk has been removed using a N-to-P cross-talk correction percentage of 5%. In this regard, the N-to-P cross-talk percentage may be derived in a manner such as described herein in connection with FIG. 4 using a purified influenza A virus particle sample fluid having a single stain appropriate for nucleic acid detection.

Figure 5B:
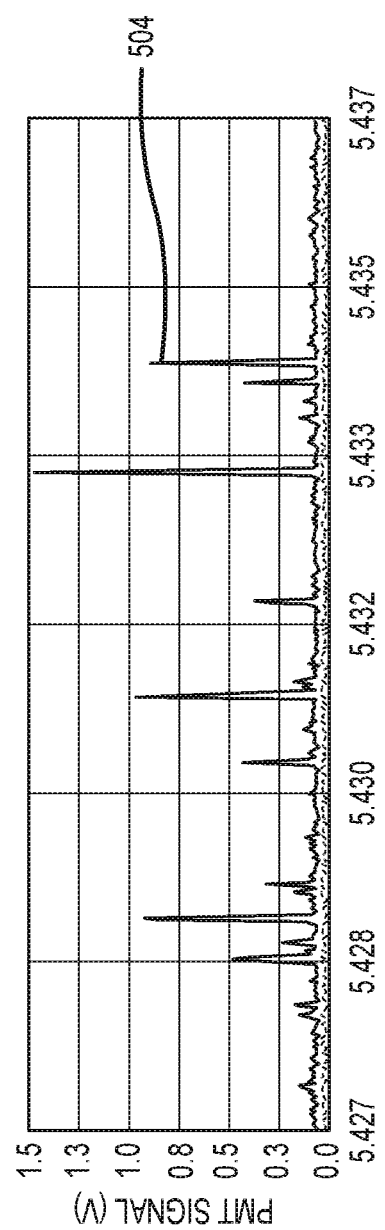

FIG. 5B depicts an exemplary corrected P-channel signal data trace 504 in which cross-talk has been removed using a P-to-N cross-talk correction percentage of 26%. In this regard, the P-to-N cross-talk percentage may be derived in a manner such as described herein in connection with FIG. 4 using a purified influenza A virus particle sample fluid having a single stain appropriate for protein detection.

Referring again to FIG. 3, in step 340 of method 300, one or more batches of data points are selected from the response data for subsequent batch processing. In an implementation where there are first and second time series signal data traces included in the response data, successive batches of data points that correspond in time (e.g., batches that represent the same time interval of their respective trace) may be selected from among the first plurality of data points comprising the first time series signal data trace and the second plurality of data points comprising the second time series signal data trace. More than one batch of data points may be selected from each time series signal data trace for subsequent batch processing, with each batch of data points that is selected from a plurality of data points comprising a particular trace being selected from a different time interval of its respective trace. In selecting the batch(es) of data points, a predetermined number of data points may be chosen from each plurality of data points comprising a time series signal data trace. The predetermined number of data points is chosen to provide a window of the respective time series signal data trace from which the data points are selected having a time period over which baseline drift is limited. In this regard, it has been found that a predetermined number of about 10,000 data points may be appropriate.

In step 350, each batch of data points is separately processed. In one implementation, the separate batch processing of each batch of data points may proceed in accordance with steps 352, 354, 356 and 358. In step 352, a batch-specific noise characteristic is determined for the batch of data points. In step 354, a batch-specific signal peak threshold is determined for the batch of data points as a function of the batch-specific noise characteristic. In step 356, signal peaks in the batch of data points indicative of the presence of a particle attribute in the sample fluid are identified using threshold criteria including the batch-specific signal peak threshold. In step 358, an assessment is made as to whether the identified signal peaks within the batch of data points are anomalous. An anomalous peak may, for example, be one with a height that exceeds the batch-specific signal peak threshold by too much as well one that is either too wide or too narrow when compared with appropriate maximum and minimum peak width filters.

Step 352 in which a batch-specific noise characteristic is determined for the batch of data points may involve determining an asymmetric Gaussian distribution fit to a portion of a histogram of the data points of the batch. In this regard, the portion of the histogram asymmetrically excludes high magnitude data points relative to low magnitude data points. In one implementation, the portion of the histogram may include data points of magnitude up to an added increment above a base magnitude corresponding with an identified maximum for the histogram and may exclude data points of magnitude larger than the added increment above the base magnitude. Further, the portion of the histogram may include data points of magnitude down to a subtracted increment below the base magnitude and may exclude data points smaller than the subtracted increment below the base magnitude, with the added increment being smaller than the subtracted increment. To further provide desired asymmetry, the subtracted increment may be at least two times as larger or more than the added increment.

In one implementation, the subtracted increment may be no smaller than three times a unit increment that is equal to a magnitude difference between the base magnitude and a half-magnitude that is smaller than the base magnitude and corresponds with a half number frequency on the histogram relative to a number frequency of the base magnitude. The base magnitude may, for example, correspond to a mean value $\mu$ of the data points of the distribution, the magnitude difference between the base magnitude and the half magnitude may correspond to a standard deviation of the data points of the distribution, and the added and subtracted increments may, for example, be based on the standard deviation $\sigma$ of the data points of the distribution. In one implementation, the added increment may be $1\sigma$ and the subtracted increment may be $5\sigma$.

Additionally, the histogram may comprise a series of data bins, with each data bin containing all data points in the batch within a fixed range of magnitudes. In this regard, the base magnitude may correspond with a magnitude within the range of the bin that includes a maximum number frequency of data points of all the bins, the data points may have a magnitude expressed in volts and the range of each bin may be no larger than 0.03 volts. In one implementation, the series of data bins may include at least one-hundred of the data bins.

Step 354 in which a batch-specific signal peak threshold is determined as a function of the batch-specific noise characteristic may involve setting the signal peak threshold based on the mean $\mu$ of the asymmetric Gaussian distribution fit plus an increment. For example, the batch-specific signal peak threshold may be set to be the greater of the mean $\mu$ of the asymmetric Gaussian distribution fit plus three times the standard deviation $\sigma$ of the asymmetric Gaussian distribution fit or the mean $\mu$ of the asymmetric Gaussian distribution fit plus 0.05V, whichever is greater (e.g., signal peak threshold is no smaller than $\mu+3\sigma$ or $\mu+0.05V$). Additionally, in one specific implementation, the batch-specific signal peak threshold may be set to be the greater of the mean $\mu$ of the asymmetric Gaussian distribution fit plus five times the standard deviation $\sigma$ of the asymmetric Gaussian distribution fit or the mean $\mu$ of the asymmetric Gaussian distribution fit plus 0.1V, whichever is greater (e.g., signal peak threshold is no smaller than $\mu+5\sigma$ or $\mu+0.1V$). Basing the batch-specific signal peak threshold on the mean $\mu$ of the asymmetric Gaussian distribution fit plus a fixed voltage may be applied where the standard deviation $\sigma$ of the asymmetric Gaussian distribution fit is particularly small and would lead to a signal peak threshold that would eliminate most, if not all, signal peaks if the signal peak threshold is based upon mean $\mu$ plus some multiple of the standard deviation $\sigma$ of the asymmetric Gaussian distribution fit.

Figure 6A:
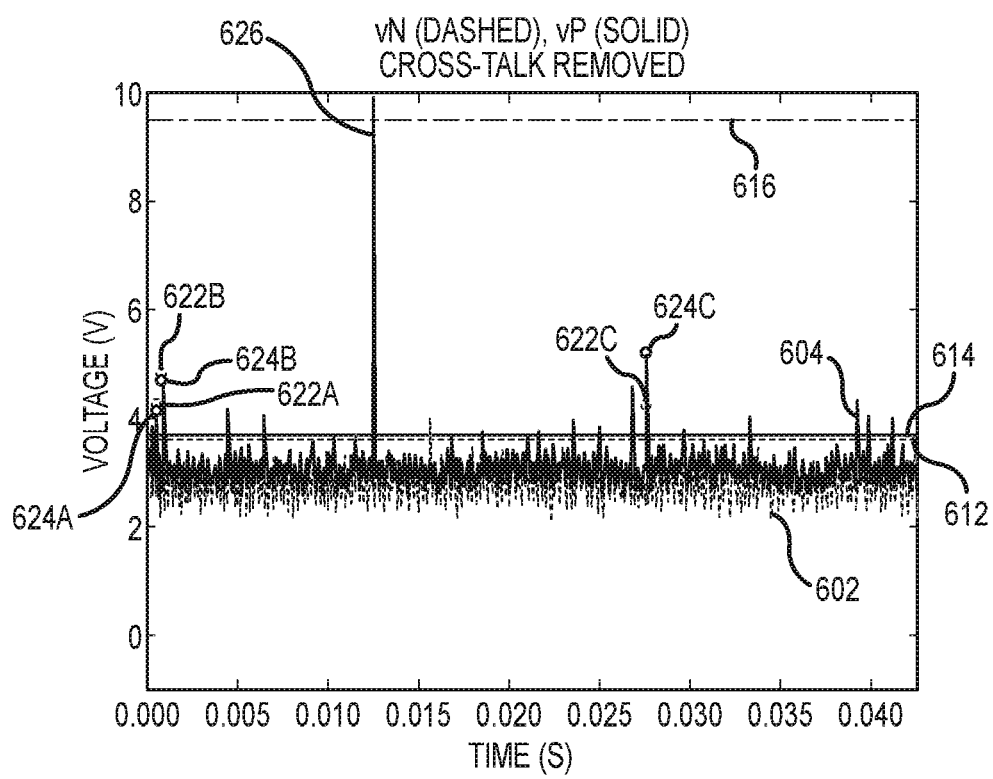
FIG. 6A is a time series plot showing a batch of 10,000 data points from a first time series signal data trace and a batch of 10,000 data points from a second time series signal data trace over corresponding time intervals.

By way of example, FIG. 6A shows a representative batch of 10,000 data points from the nucleic acid channel trace 602 and the protein channel trace 604 plotted versus time. Respective signal peak thresholds 612, 614 for the nucleic acid channel trace 602 and the protein channel trace 604 are indicated by the horizontal dashed lines, with the signal peak threshold 612 for the nucleic acid channel trace 602 being slightly lower than the signal peak threshold 614 for the protein channel trace 604 in the illustrated example. In other situations, the nucleic acid channel trace 602 signal peak threshold 612 may be slightly or significantly more than the protein channel trace 604 signal peak threshold 614 or the nucleic acid channel trace 602 signal peak threshold 612 may significantly less than the protein channel trace 604 signal peak threshold 614. A clipping threshold 616 is shown by the horizontal line at 9.5V. The clipping threshold may be used to identify peaks that are anomalous because their height exceeds the applicable signal peak threshold 612, 614 by too much. Three signal peaks 622A-622C are marked by circles in the nucleic acid channel trace 602 that correspond in time with three signal peaks 624A-624C marked by circles in the protein channel trace 604. A single clipped peak 626 in the protein channel 604 is also shown.

Figure 6B:
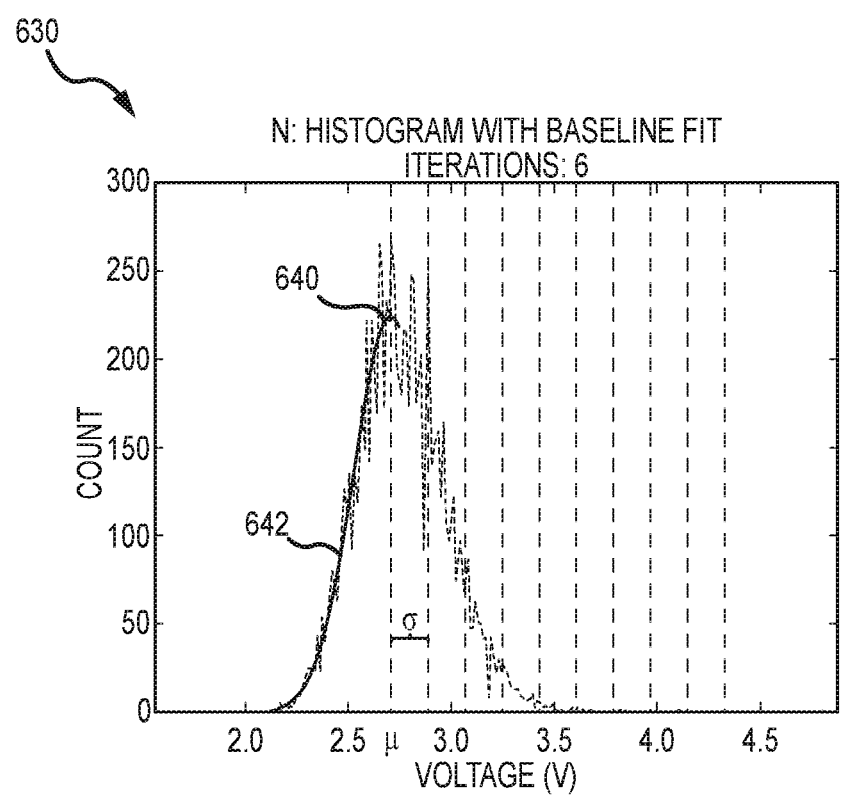
FIG. 6B is a histogram plot for the first time series signal data trace shown in FIG. 6A.

FIG. 6B shows a histogram 630 for a time series signal data trace such as the nucleic acid channel trace 602 of FIG. 6A, showing a clear normally distributed noise peak 640. The asymmetric Gaussian distribution fit is also shown referenced by numeral 642, and integer multiples of the standard deviation $\sigma$ away from the mean $\mu$ are indicated by the vertical dashed lines. As depicted, less than the entire range of the histogram 600 has been used in computing the asymmetric Gaussian distribution fit 642. In this regard, data points with a voltage below a subtracted increment from the mean $\mu$ (e.g., below $\mu-5\sigma$) and above an added increment from the mean $\mu$ (e.g., above $\mu+1\sigma$) have been excluded in computing the asymmetric Gaussian distribution fit 642.

Referring again to FIG. 3, in step 356, signal peaks are identified in each batch of data points. The signal peaks may be identified by comparing the voltage values of the data points in each batch with the appropriate signal peak threshold for such batch. For example, the data points in the nucleic acid channel trace 602 may be compared with the batch-specific signal peak threshold 612 for the nucleic acid channel trace 602 with consecutive points exceeding the batch-specific signal peak threshold 612 being considered to comprise a signal peak in the nucleic acid channel trace 602 indicative of the presence of a particular nucleic acid particle in the sample fluid. Likewise, the data points in the protein channel trace 604 may be compared with the batch-specific signal peak threshold 614 for the protein channel trace 604 with consecutive points exceeding the batch-specific signal peak threshold 614 being considered to comprise a signal peak in the protein channel trace 604 indicative of the presence of a particular protein particle in the sample fluid.

In step 358 of the method 300, an assessment is made as to whether or not an identified peak is an anomalous peak. In one implementation of the method 300, step 358 may not be included in which case no assessment is made as to whether any of the identified peaks are anomalous. In implementations of the method 300 including step 358, each data point comprising an identified peak in the batches of data points is compared with an anomaly threshold. One example of an anomaly threshold is the clipping threshold 616 shown in FIG. 6A. Other examples of anomaly thresholds include minimum and maximum peak widths. If the data point(s) comprising an identified peak exceed the anomaly threshold, such identified peak is considered to be anomalous (e.g., considered a clipped peak where the anomaly threshold is a clipping threshold). Anomalous peaks may be rejected as peaks considered indicative of the presence of a particle attribute and excluded from further consideration in the method 300. For example, each of the corresponding in time signal peaks 622A-622C, 624A-624C depicted in FIG. 6A are considered signal peaks because they exceed their respective nucleic acid channel trace 602 and protein channel trace 604 signal peak thresholds 612, 614 without exceed the clipping threshold 616; whereas, the clipped peak 626 is considered anomalous because it also exceeds the clipping threshold 616 in addition to the signal peak threshold 614 for the protein channel trace 604.

In step 370, a comparison is made between times of occurrence of non-anomalous identified signal peaks in the separately batch-processed batches of data points from the first signal data trace and the second signal data trace over the same time interval. In step 372, the non-anomalous signal peaks that coincide in time may be recorded as the presence of a target particle in the sample fluid. For example, each of the corresponding in time signal peaks 622A-622C, 624A-624C depicted in FIG. 6A may be recorded as the presence of a target particle (e.g., an influenza virus) since non-anomalous signal peaks indicating the presence of a first particle attribute (e.g., a nucleic acid) and a second particle attribute (e.g. a protein) in the sample fluid have temporal coincidence.

In step 374, for each batch of data points that is separately batch processed in step 350, an update is made to a set of collective statistics for the time series signal data trace(s). The collective statistics that are updated include characteristics of the identified signal peaks from multiple batches. For example, the characteristics of the identified signal peaks may comprise one or more of a start point associated with an identified peak, an end point associated with an identified peak, a width of an identified peak, a maximum value of an identified peak, a time of the maximum value of an identified peak, an indicator of whether an identified peak was anomalous, and a count of the number of coinciding in time signal peaks recorded as the presence of the target particle.

In step 380, a concentration of the target particle may be calculated based on the collective statistics (e.g., the updated count of the number of coinciding in time signal peaks recorded as the presence of the target particle) and a measured flow rate of the sample fluid to the flow cell. In this regard, when conducting the flow cytometry investigation, the flow rate of sample fluid through the flow cell may be maintained at or below a desired maximum flow rate in order to help facilitate the accurate identification of target particles in accordance with the method 300. Although other maximum flow rates may be appropriate, in one implementation the maximum flow rate may be 1000 nanoliters/minute.

In step 382, results of the flow cytometry investigation may be displayed. In this regard, the results may include the calculated concentration of the target particle. The results that are displayed may also include the collected statistics. In one implementation, the results may be displayed contemporaneous to the flow cytometry investigation (e.g., by displaying the results on a display screen of the flow cytometer instrument and/or a display of a computer system interfaced with the flow cytometer instrument).

Figure 7:
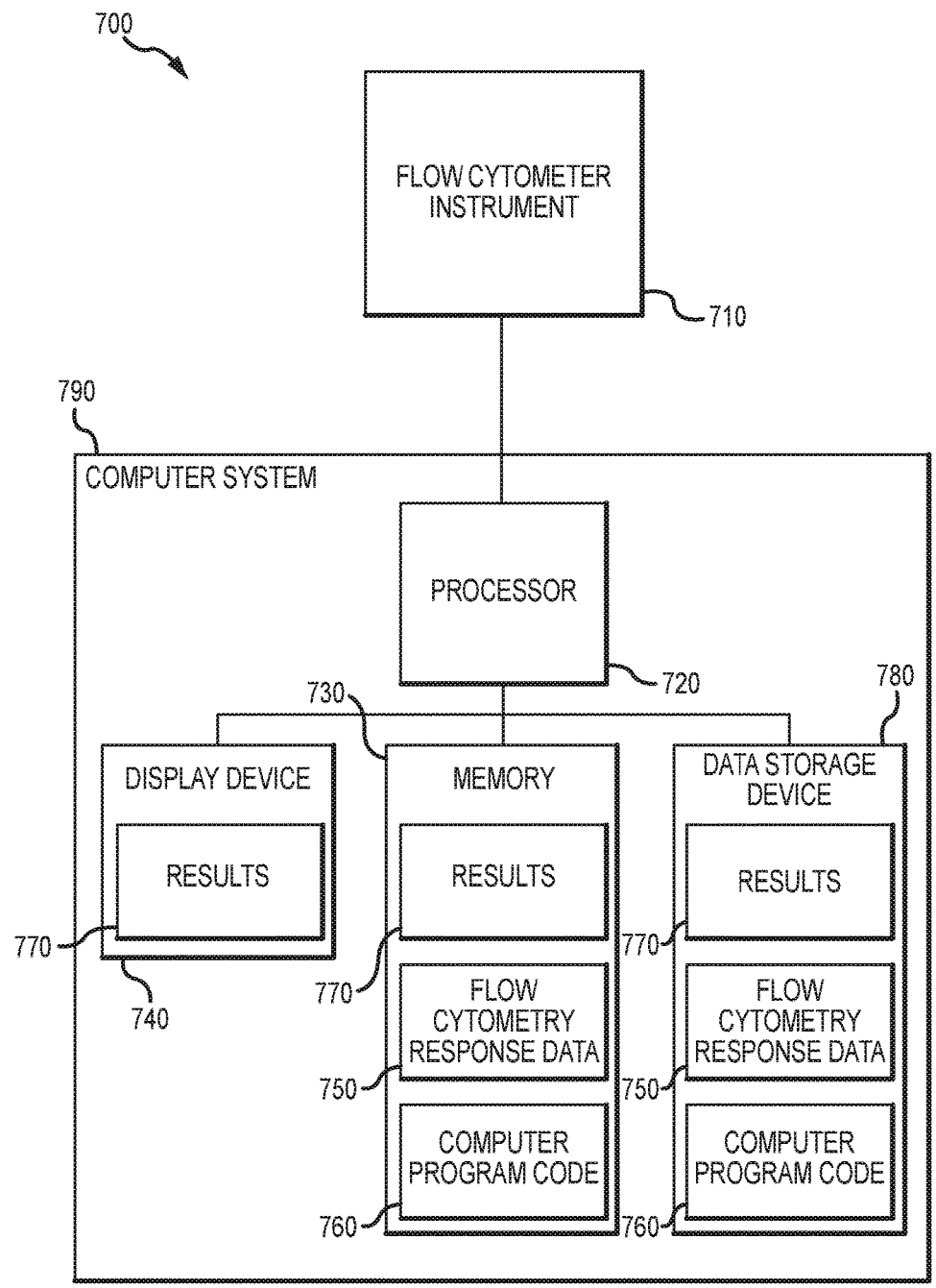
FIG. 7 is a block diagram of one embodiment of a flow cytometer system.

FIG. 7 is a block diagram representation of one embodiment of a flow cytometer system 700. The flow cytometer system 700 includes flow cytometer instrument 710, a processor 720, a memory 730 and a display device 740. The flow cytometer instrument 710 may, for example, comprise a flow cytometer instrument 100 having a flow cytometer internal assembly 180 within an enclosure 102 such as depicted and described in connection with FIGS. 1A-1B and 2A-2B. Regardless of its configuration, the flow cytometer instrument 710 is operable to output flow cytometry investigation response data 750, where the response data 750 comprises one or more time series signal data traces corresponding with detection during the flow cytometry investigation of light from the sample fluid in one or more wavelength ranges indicative of the presence of one or more particle attributes in a sample fluid being undergoing flow cytometry investigation. The response data 750 may be stored in the memory 730. The processor 720 is operable to receive the flow cytometry response data 750 output by the flow cytometer instrument 710. In this regard, the processor 720 may receive the response data 750 directly from the flow cytometer instrument 710 as it is output and/or from the memory 730 where the response data 750 has been stored. The processor 720 is operable to process the response data 750 to evaluate particle attributes in the sample fluid (e.g., to identify the presence of nucleic acid and protein attributes indicative of a target particle such as an influenza virus). The processor 720 may process the response data 750 by performing one or more of the steps of a method 300 such as depicted and described in connection with FIG. 3. In this regard, the processor may comprise a general purpose microprocessor, and computer executable program code 760 may be stored on the memory 730 and executed by the processor 720 to accomplish processing of the response data 750. It may also be possible for the processor 720 to comprise one or more application specific integrated circuits (ASICs) and/or field programmable gate arrays (FPGAs) in combination with a general purpose microprocessor that together accomplish processing of the response data 750 or one or more ASICs and/or FPGAs without a general purpose microprocessor that accomplish processing of the response data 750. Results 770 of the processing of the response data 750 accomplished by the processor 720 may be displayed on the display device 740. The results 770 may be displayed as the flow cytometry investigation is ongoing and/or after it is completed. The results 770 may also be stored in the memory 730 and/or on a non-volatile data storage device 780 (e.g. a hard disc, an optical disc, a flash memory, etc.) that may be included in the flow cytometry system 700. In addition to storing the results 770, the non-volatile data storage device may also store the response data 750 (e.g., in raw and cross-talk corrected forms) and/or the computer executable program code 760. In one implementation such as depicted, the processor 720, memory 730, display device 740 and data storage device 780 comprise a computer system 790 separate from the flow cytometer instrument 710 and interfaced therewith for communication therebetween. In this regard, the computer system 790 may, for example, comprise a laptop, desktop, notebook, or touch pad computing device, and may have additional components not depicted such as a keyboard, mouse and/or touch screen/pad input device. In other implementations, one or more of the processor 720, memory 730, display device 740, and data storage device 780 may be incorporated within the flow cytometer instrument 710.

Deviations may be made from the specific embodiments disclosed in the specification without departing from the spirit and scope of the invention. For example, at least some of the functionalities performed by many of the processes, devices and modules etc. discussed herein may be performed by other modules, devices, processes, etc. The illustrations and discussion herein has only been provided to assist the reader in understanding the various aspects of the present disclosure.

Furthermore, the various utilities disclosed herein (e.g., the method of evaluating particle attributes in a sample fluid subjected to flow cytometry investigation in a flow cytometer instrument) are not limited to being used in the context of the specific flow cytometer instrument described herein.

A computer program (also known as a program, software, software application, script, or code) used to provide the functionality described herein (such as to provide one or more steps of the method of evaluating particle attributes in a sample fluid subjected to flow cytometry investigation in a flow cytometer instrument) may be written in any form of programming language, including compiled or interpreted languages, and may be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by an information flow network.

The block diagrams, processes, protocols and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Generally, the elements of a computer are a processor for performing instructions and one or more memory devices for storing instructions and data. The techniques described herein may be implemented by a computer system configured to provide the functionality described.

While this disclosure contains many specifics, these should not be construed as limitations on the scope of the disclosure or of what may be claimed, but rather as descriptions of features specific to particular embodiments of the disclosure. Certain features that are described in this specification in the context of separate embodiments and/or arrangements can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Additionally, the foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A flow cytometer system comprising:
   a flow cytometer instrument operable to output flow cytometry investigation response data, the response data comprising a time series signal data trace corresponding with detection during the flow cytometry investigation of light from the sample fluid in a wavelength range that is indicative of the presence of a particle attribute in the sample fluid; and
   a processor operable to receive the flow cytometry response data output by the flow cytometer instrument, the processor being further operable to separately batch process a plurality of different time interval batches of data points of the time series signal data trace to:
      determine a batch-specific noise characteristic for said batch of data points;
      determine a batch-specific signal peak threshold for said batch of data points as a function of the batch-specific noise characteristic;
      identify signal peaks in said batch of data points indicative of the presence of the particle attribute in the sample fluid using threshold criteria including the batch-specific signal peak threshold; and
      update a set of collective statistics for the time series signal data trace including characteristics of the identified signal peaks from multiple batches;
   wherein said processor is operable in said batch processing to calculate a concentration of particles using the collective statistics and a measured flow rate of the sample fluid.

2. A system according to claim 1, wherein the characteristics of the identified signal peaks from multiple batches comprise one or more of a start point associated with an identified peak, an end point associated with an identified peak, a width of an identified peak, a maximum value of an identified peak, a time of the maximum value of an identified peak, and an indicator of whether an identified peak was anomalous.

3. A system according to claim 1, wherein said processor is operable in said batch processing to:
   assess whether an identified peak is an anomalous peak; and
   reject anomalous peaks as peaks indicative of presence of the particle attribute.

4. A system according to claim 3, wherein said processor is operable in said batch processing to:

assess whether an identified peak is an anomalous peak by, for each data point above the batch-specific signal peak threshold, comparing a value of the data point with an anomaly threshold that is greater than the batch-specific signal peak threshold, wherein data points having values above the anomaly threshold are considered to comprise an anomalous peak.

5. A system according to claim 3, wherein the characteristics of the identified signal peaks from multiple batches comprise one or more of a start point associated with an identified peak, an end point associated with an identified peak, a width of an identified peak, a maximum value of an identified peak, a time of the maximum value of an identified peak, and an indicator of whether an identified peak was anomalous.

6. A system according to claim 1, wherein the flow cytometer instrument further comprises:
a flow cell;
at least one light source;
a fluid pressurizing device operable to pressurize the sample fluid to direct the sample fluid through the flow cell where the sample fluid is subjected to an excitation light from said at least one light source;
one or more photodetectors operable to separately detect at least two different response light wavelengths emitted from the sample fluid in the flow cell; and
a flow sensor operable to measure a flow rate of the sample fluid in the flow cell; and wherein:
the flow cytometer instrument maintains a flow rate of sample fluid flow through the flow cell during the flow cytometry investigation of not more than 1000 nanoliters/minute; and
the sample fluid comprises virus particles.

7. A system according to claim 6, wherein said processor is operable to perform said batch processing contemporaneous to investigation of the sample fluid in the flow cell, and wherein:
said system further comprises a display device;
said processor is further operable to display results of said batch processing on said display device contemporaneous to investigation of the sample fluid in the flow cell; and
the results include said concentration of particles calculated using collective statistics and a measured flow rate of the sample fluid in the flow cell.

8. A system according to claim 1, wherein to determine a batch-specific noise said processor is operable to:
determine an asymmetric Gaussian distribution fit to a portion of a histogram of the data points of the batch, wherein the portion of the histogram asymmetrically excludes high magnitude data points relative to low magnitude data points.

9. A system according to claim 8 wherein:
the portion of the histogram includes data points of magnitude up to an added increment above a base magnitude corresponding with an identified maximum for the histogram and excludes data points of magnitude larger than the added increment above the base magnitude;
the portion of the histogram includes data points of magnitude down to a subtracted increment below the base magnitude and excludes data points smaller than the subtracted increment below the base magnitude; and
the added increment is smaller than the subtracted increment.

10. A system according to claim 9, wherein the subtracted increment is at least two times as large as the added increment.

11. A system according to claim 10, wherein the subtracted increment is no smaller than three times a unit increment that is equal to a magnitude difference between the base magnitude and a half-magnitude that is smaller than the base magnitude and corresponds with a half number frequency on the histogram relative to a number frequency of the base magnitude.

12. A system according to claim 11, wherein the histogram comprises a series of data bins, wherein each said data bin contains all data points in the batch within a fixed range of magnitudes and the base magnitude corresponds with a magnitude within the range of a said bin that includes a maximum number frequency of data points of all said bins, wherein the data points have a magnitude expressed in volts and the range of each said bin is no larger than 0.03 volt, and wherein the series of data bins includes at least 100 of said data bins.

13. A system according to claim 8, wherein the batch-specific signal peak threshold is not smaller than the mean of the asymmetric Gaussian distribution fit plus three times the standard deviation of the asymmetric Gaussian distribution fit.

14. A system according to claim 8, wherein the batch-specific signal peak threshold is not smaller than the mean of the asymmetric Gaussian distribution fit plus 0.05V.

15. A system according to claim 1, wherein the sample fluid comprises virus particles.

16. A system according to claim 1, wherein:
the time series signal data trace comprises a first time series signal data trace, the particle attribute comprises a first particle attribute and the light comprises first light from the sample fluid in a first wavelength range that is indicative of the presence of the first particle attribute;
the response data further comprises a second time series signal data trace corresponding with detection during the flow cytometry investigation of light from the sample fluid in a second wavelength range that is indicative of the presence of a second particle attribute in the sample fluid; and
the processor is further operable to separately batch process a plurality of different time interval batches of data points of the second time series signal data trace, wherein time intervals of each successive batch of data points of the second time series signal data trace correspond in time with time intervals of each successive batch of data points of the first time series signal data trace, and wherein said processor separately batch processes the plurality of different time interval batches of data points of the second time series signal data trace to:
determine a batch-specific noise characteristic for said batch of data points of the second time series signal data trace;
determine a batch-specific signal peak threshold for said batch of data points of the second time series signal data trace as a function of the batch-specific noise characteristic for said batch of data points of the second time series signal data trace; and
identify signal peaks in said batch of data points of the second time series signal data trace indicative of the presence of the second particle attribute in the sample fluid using threshold criteria including the batch-specific signal peak threshold.

17. A system according to claim 16, wherein said processor is further operable to:
  compare times of occurrence of the identified signal peaks in said separately batch-processed batches of data points of the first and the second time series signal data traces.

18. A system according to claim 17, wherein said processor is further operable to:
  record as the presence of a target particle a temporal coincidence of identified signal peaks in the batches of data points of the first and the second time series signal data traces.

19. A system according to claim 18, wherein the first light comprises light in a first wavelength range that is a fluorescent emission of a first fluorescent stain, and wherein the second light comprises light in a second wavelength range that is a fluorescent emission of a second fluorescent stain.

* * * * *